United States Patent [19]
Blechta et al.

[11] Patent Number: 5,273,641
[45] Date of Patent: Dec. 28, 1993

[54] ELECTRODE AND METHOD FOR MEASURING LEVELLING POWER

[75] Inventors: Vladimir K. Blechta; Zheng Z. Wang; Dale W. Krueger, all of Sudbury, Canada

[73] Assignee: Inco Limited, Toronto, Canada

[21] Appl. No.: 979,205

[22] Filed: Nov. 20, 1992

Related U.S. Application Data

[60] Division of Ser. No. 911,754, Jul. 10, 1992, Pat. No. 5,236,571, which is a continuation-in-part of Ser. No. 822,726, Jan. 21, 1992, abandoned.

[51] Int. Cl.$^5$ ............................................. G01N 27/26
[52] U.S. Cl. ..................................... 204/434; 205/83; 205/103
[58] Field of Search ................. 205/83, 103; 204/402, 204/434

[56] References Cited

U.S. PATENT DOCUMENTS 4,146,437  3/1979  O'Keefe .............................. 205/103

*Primary Examiner*—John Niebling
*Assistant Examiner*—Bruce F. Bell
*Attorney, Agent, or Firm*—Blake T. Biederman; Edward A. Steen

[57] ABSTRACT

The invention provides an apparatus and method for determining levelling power of an electrolyte. An anode and cathode are immersed in the electrolyte. The cathode has a plating surface for electrodeposition of a metal from the electrolyte. The plating surface has a peak region and a base region separated and electrically isolated by an insulator. The peak region has a greater tendency to electrodeposit the metal per unit surface area than the base region. The anode and cathode are placed in a test cell or suspended in a commercial electrodeposition cell. A means for applying current between said anode and said cathode is used for causing the metal from the electrolyte to electrodeposit on the plating surface of the cathode. The current from plating on the peak region and the base region are measured separately to determine levelling power of an electrolyte.

9 Claims, 4 Drawing Sheets

A = 10 PPM LIGNOSULFONATE
B = 20 PPM LIGNOSULFONATE
C = 50 PPM LIGNOSULFONATE
D = 100 PPM LIGNOSULFONATE

A = 0 PPM. THIOUREA
B = 1 PPM. THIOUREA
C = 2 PPM. THIOUREA
D = 5 PPM. THIOUREA
E = 50 PPM. THIOUREA

ELECTRODE AND METHOD FOR MEASURING LEVELLING POWER

This is a divisional of co-pending application Ser. No. 07/911,754 filed on Jul. 10, 1992, now U.S. Pat. No. 5,236,571. Application Ser. No. 07/911,754 was a continuation-in-part of co-pending application Ser. No. 07/822,726 filed Jan. 21, 1992, now abandoned.

FIELD OF INVENTION

This invention is related to the field of measuring the ability of addition agents to prevent formation of rough and porous surfaces and nodules during electrodeposition.

BACKGROUND OF THE ART AND PROBLEM

The process of electrodeposition is widely used commercially in processes such as electrorefining, electrowinning and electroplating. In commercial electrodeposition operations organic and/or inorganic addition agents are added directly to electrolytic solutions. The addition agents control uniformity of metal deposition on a cathode. When the addition agents are out of balance for proper electrodeposition, the metal deposit forms rough porous surfaces and nodules which encapsulate impurities contained in the electrolyte. Improper deposition typically greatly reduces the value of the product due to impurities mechanically imbedded in the rough cathode surface.

Copper electrorefineries around the world typically use a combination of several addition agents to control electrorefining. Addition agents used for electrorefining include animal glue, thiourea, lignin sulfonate, alkyl sulfonate and chloride ion. Positively charged addition agents such as animal glue are drawn by electrochemical forces to the negatively charged cathode. Positively charged addition agents are more strongly attracted to increased current density regions of peaks or nodules formed on a cathode. The increased concentration of addition agents on peaks or nodules slows down the metal electrodeposition and levelling takes place.

Advantageously, an addition agent such as glue is preferentially adsorbed on the peak or nodule to form a resistance layer which locally increases over-potential and levelling on the cathode surface takes place. If excess addition agent is present, the addition agent absorbs over an entire cathode surface which causes a loss of levelling effect. If insufficient addition agent is present, growth on peaks and nodules is not prevented and the peaks and nodules grow in an uncontrolled accelerated manner. Typical optimum concentration of addition agents is in the parts per million range. Unfortunately, concentrations of addition agents are very difficult to measure in a simple and accurate manner. Furthermore, several addition agents break down into multiple components and eventually lose levelling effect.

Typical copper electrorefinery addition agent systems are complicated and include a combination of three or more addition agents. As a result of high interactions between addition agents, levelling effects of new combinations of levelling agents are unpredictable. To evaluate an addition agent system time consuming laboratory or pilot plating experiments have been required. A typical experiment requires 7 to 14 days to complete. It would require about 5 to 10 years (without simultaneous experiments) to investigate every combination of a system of four addition agents each at four different concentrations.

T. Zak, in "Microlevelling During Electrolytic Deposition of Metals," Translation of the Institute of Metal Finishing, Vol. 49, (1971), pp. 220-26, discloses a laboratory set up designed for attempting to measure potential difference of cathodes. Laboratory equipment of Zak used cathodes having alternating plates insulated and spaced 0.02 mm apart and every second cathode was either 0.01 or 0.02 mm closer to an anode. The set up of Zak was unable to record a difference in potential between protruding and recessed electrode depending upon any addition agent used. In contrast, several techniques have been successfully developed to monitor addition agent concentrations in electrolyte. Langner et al, in U.S. Pat. No. 4,834,842, describe a technique of measuring effectiveness of addition agents by measuring kinetics of cathode polarization under predetermined conditions. Other techniques described in the literature have measured cathode polarization in an attempt to optimize plating conditions. These cathode polarization techniques are not capable of measuring the ability of an addition agent or a combination of addition agents to alter cathode levelling.

It is an object of this invention to provide an apparatus and method for evaluating the ability of an addition agent to improve cathode surface during electrodeposition.

It is a further object of this invention to provide a quick and effective method for evaluating addition agents and their combination for cathode levelling.

It is a further object of this invention to provide a method for controlling levelling power of electrolytes to prevent the formation of a rough nodulated and contaminated surface by adjusting the addition agents concentration.

SUMMARY OF THE INVENTION

The invention provides an apparatus and method for determining levelling power of an electrolyte. An anode and cathode are immersed in the electrolyte. The cathode has a plating surface for electrodeposition of a metal from the electrolyte. The plating surface has a peak region and a base region separated and electrically isolated by an insulator. The peak region has a greater tendency to electrodeposit the metal per unit surface area than the base region. The anode and cathode are placed in a test cell or suspended in a commercial electrodeposition cell. A means for applying current between said anode and said cathode is used for causing the metal from the electrolyte to electrodeposit on the plating surface of the cathode. The current used in plating metal on the peak region and the base region are measured separately to determine levelling power of the electrolyte.

DESCRIPTION OF PREFERRED EMBODIMENT

It has been discovered that a newly developed electrode system has the ability to measure the levelling effect of addition agents in electrolyte. The electrode system includes a cathode which contains a peak region (or several peak regions) and a flat base or valley region. Current flow is measured separately for peak and base regions to quickly determine the levelling effect of various combinations of addition agents.

Figure 1:
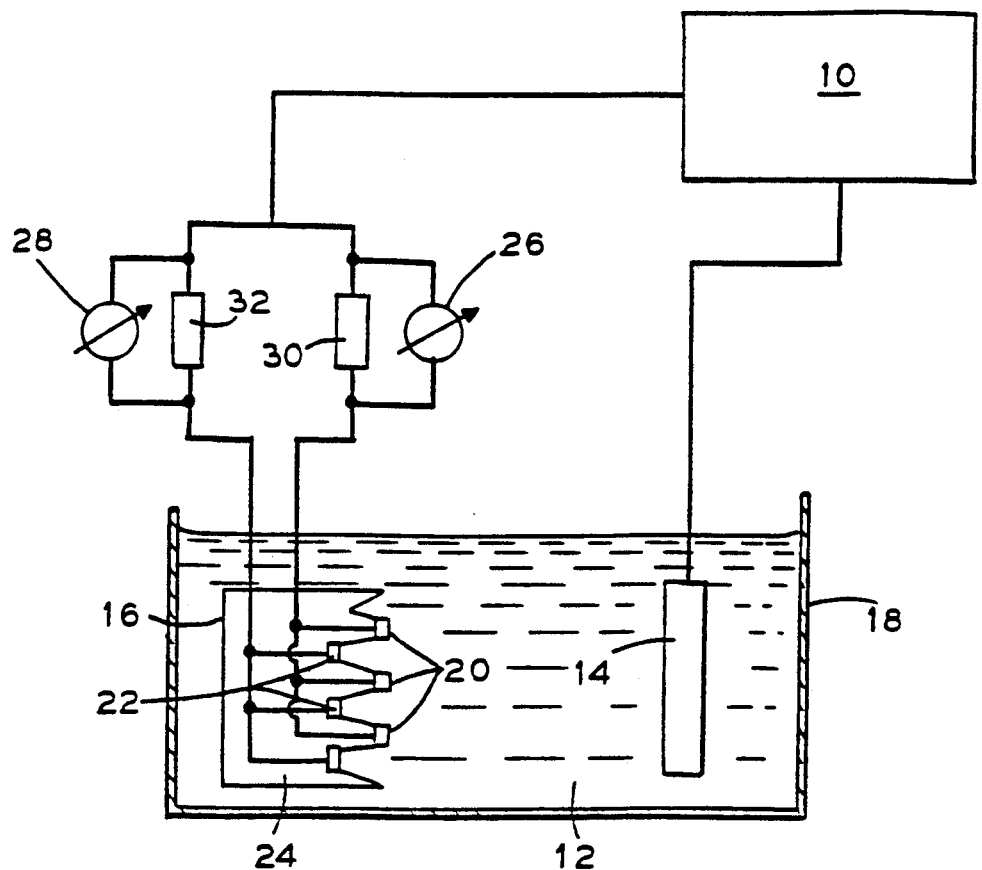
FIG. 1 is a schematic diagram of an apparatus for measuring levelling power.

Referring to FIG. 1, the apparatus includes galvanostat 10 which generates a constant current through electrolyte 12 between anode 14 and cathode 16. Electrolyte 12, anode 14 and cathode 16 are all contained in test cell 18. As an alternative to test cell 18, any means to hold anode 14 and cathode 16 in electrolyte 12 may be used. For example, anode 14 and cathode 16 may be simply suspended by clamps, bolts or wires in a commercial electrolytic solution. Cathode 16 is of a "sandwich" structure having three peak regions 20 and three base regions 22 placed upon an insulating structure 24. Insulating structure 24 may be constructed out of any insulating material such as plastic or ceramic. Typically, nodules arising during electrorefining and electrowinning have a height of 0.5 to 1.5 mm. Peak regions 20 were placed 4 mm closer to anode 14 to create a current density adjacent the peak regions 20 that was stronger than the current density adjacent the base regions 22. Preferably, peak regions are at least 0.5 mm closer than base regions to the anode to provide a sufficient current density difference. Advantageously, peak regions are spaced at least 1 mm apart to provide additional accuracy. Most advantageously, peak regions of the cathode are spaced 2 to 5 mm closer to the anode than the base region to simulate nodular effect. Alternatively, geometry such as a projecting cathode may be used to create a greater tendency for metal to electrodeposit per unit surface area on peak regions 20 than base regions 22. For purposes of the invention, unit surface area is defined as total plating surface. Galvanostat 10 provides sufficient current to electrodeposit metal on the peak regions 20 and base regions 22. Alternatively, other means for electrodepositing metal on cathode base region 22 and peak region 20 may be studied. For example, systems that periodically reverse current to stir electrolyte may be studied. When using test cell 18, electrolyte 12 is most preferably heated to within about 5° C. of the electrolyte to be tested. Test cell 18 may be heated by any means for heating a test cell such as a hot plate.

During electrodeposition, current flowing to the peak regions 20 and base region 22 is determined separately with voltmeters 26 and 28 and resistors 30 and 32. Advantageously, resistors 30 and 32 have a similar resistance of about 1-5 ohms. Wiring is used to connect the base and peak regions to current measuring devices. From the measured voltage and resistance, current may be calculated. Alternatively, current may be directly measured with ammeters. Most advantageously, current flowing to the peak regions and total current flowing to the base and peak regions is measured. It is recognized that material electrodeposited on the peak regions is measured. It is recognized that material electrodeposited on the peak regions and material electrodeposited on the base regions may be weighed separately and compared or simply visually compared to determine levelling effect. However, it is highly advantageous to simply electrically measure current flows to determine levelling effect.

The beneficial levelling effect with and without addition agents in an electrolyte is advantageously determined with the following formula:

$$LP = \frac{It - Ip}{Ip} \times 100$$

where:
LP=Levelling Power
Ip=Current flowing to the peak electrode(s)
It=Total current flowing to the cathode The above described system models the rough surface of a cathode and provides for direct measurement of the blocking effect of addition agents on the peaks of a rough cathode. The blocking effect is expressed as a levelling power. Levelling power is measured by determining ratio of current flowing to base regions and peak regions. Levelling power may be measured in 15 to 30 minutes. After 15 to 30 minutes of plating, the electrolyte begins to change and peak current begins to stabilize. Most advantageously, total current over a time range is used to obtain more accurate results. For example, to study levelling power during nucleation, peak current and total current may be measured for the initial 5 minutes. A measurement of 5 minutes until stabilization of peak current may be used to study electrodeposition following nucleation. When peak current stabilizes, the test is completed. After measuring levelling power of a commercial electrolyte, addition agents may be manually adjusted or automatically adjusted to optimize levelling power.

The sandwich electrode of FIG. 1 was constructed out of copper and chlorinated polyvinyl chloride (CPVC) insulating material using an adhesive. For long term use, an insulator and an adhesive that can withstand harsh environments at increased temperatures or a design that does not utilize adhesive is preferred. CPVC is a specific material that has been found to provide excellent resistance to corrosive acid environments. Cathodes 16 are preferably constructed with base regions and peak regions constructed of a stable metal such as platinum. Using a platinum cathode allows for cleaning of the anode by simply reversing polarity of galvanostat 10 to redissolve plated material into the electrolyte. Similarly, anode 14 is preferably constructed of metal deposited on the cathode or a stable metal such as platinum or lead-antimony alloy to prevent dissolution of the anode into electrolyte 12, depending upon the process studied. For example, a lead-antimony alloy is preferred for electrowinning of copper studies. Anode 14 preferably has a surface area of at least 10 times the surface area of the conductive surface area of the cathode to provide uniform current flow to the cathode.

Figure 2:
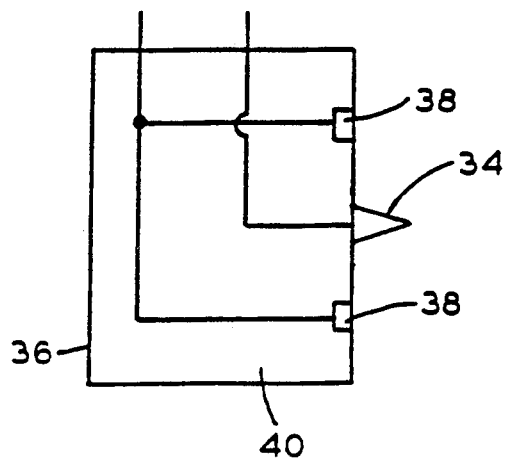
FIG. 2 is a schematic side view of an optional peak electrode having a projecting peak region.

Although cathodes preferably have flat base and peak regions, peak regions may have a projecting configuration. Referring to FIG. 2, peak region 34 of cathode 36 has a solid conical shape. Peak region 34 preferably projects toward an anode to create a greater tendency to electrodeposit metal per unit surface area. Base regions 38 are isolated from peak region 34 with insulator 40. Preferably, surface area of peak region 34 is equal to surface area of base regions 38. The advantage of the structure of FIG. 2 is that CPVC adhesive may be used to hold the entire cathode structure together.

An experimental setup was produced having a copper anode. The copper anode had a surface area of 4 cm$^2$. The cathode used had a structure similar to the cathode of FIG. 2. The cathode had 3 flat platinum base regions and 1 conically shaped peak region. The surface area of the base region and peak region were each about 0.053 cm$^2$. A CPVC material acted as an electrical insulator between the base region and the peak region. The base regions were laterally spaced 3.5 mm from the peak region. The above experimental setup was used for the following Examples.

EXAMPLE 1

A synthetic electrolyte of the following composition was used:

| | |
|---|---|
| Cu | 40 g/l |
| Ni | 20 g/l |
| H$_2$SO$_4$ | 150 g/l |
| Cl$^-$ | 20 mg/l |

Figure 3:
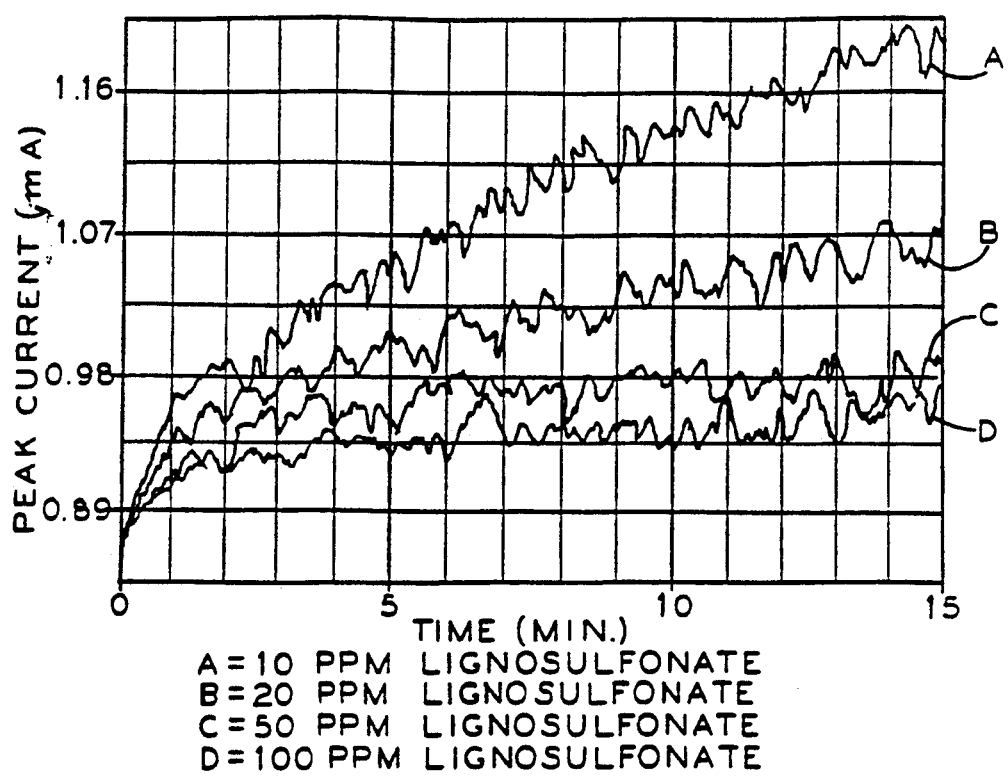
FIG. 3 is a graph of cathode peak current versus time with various concentrations of lignin sulfonate in a copper electrorefining solution.
Figure 4:
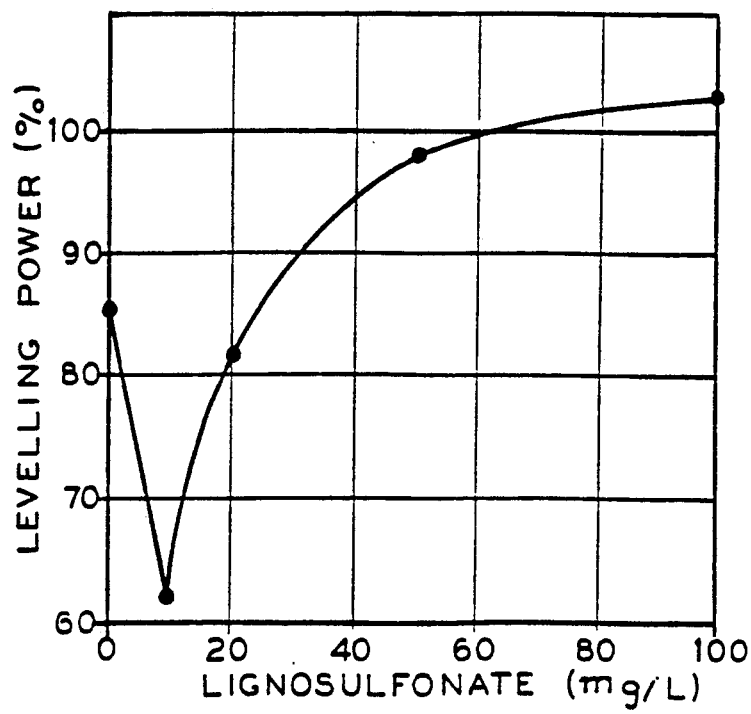
FIG. 4 is a graph of levelling power versus concentration for lignin sulfonate in a copper electrorefining solution.

The electrolyte temperature during measuring was 65° C. and the average cathode current density was 182 A/m$^2$ which simulated a commercial copper electrorefining operation. Measurements are preferably made at temperatures and current densities that simulate commercial conditions. Different amounts of Tembind TM (a lignin sulfonate produced by Temfibre Inc. of Temiscaming, Quebec) were added to the electrolyte and the cathode peak current time profile was recorded. Cathode peak current was calculated from the measured voltage and a predetermined constant resistance. The recorded current time profile is shown in FIG. 3. The results of the experiment are summarized in Table 1 and the effect of Tembind concentration on the levelling power is shown in FIG. 4. The lowest levelling power (LP) of the electrolyte in the presence of 20 mg/l Cl$^-$ is around 10 mg/l Tembind. Above 10 mg/l Tembind, the levelling power sharply rises with increased Tembind concentration and reaches its maximum at concentrations over 100 mg/l.

TABLE 1

Effect of Tembind Concentration on Cathode Peak Current and Levelling Power

| Tembind (mg/l) | Cathode Peak Current (mg/l) | Levelling Power (%) |
|---|---|---|
| 0 | 1.043 | 85.0 |
| 10 | 1.196 | 61.4 |
| 20 | 1.061 | 81.9 |
| 50 | 0.976 | 97.9 |
| 100 | 0.953 | 102.5 |

Current Density = 182A/m$^2$.
Cathode Total Current = 1.93 mA;
Plating time = 15 min.

EXAMPLE 2

Figure 5:
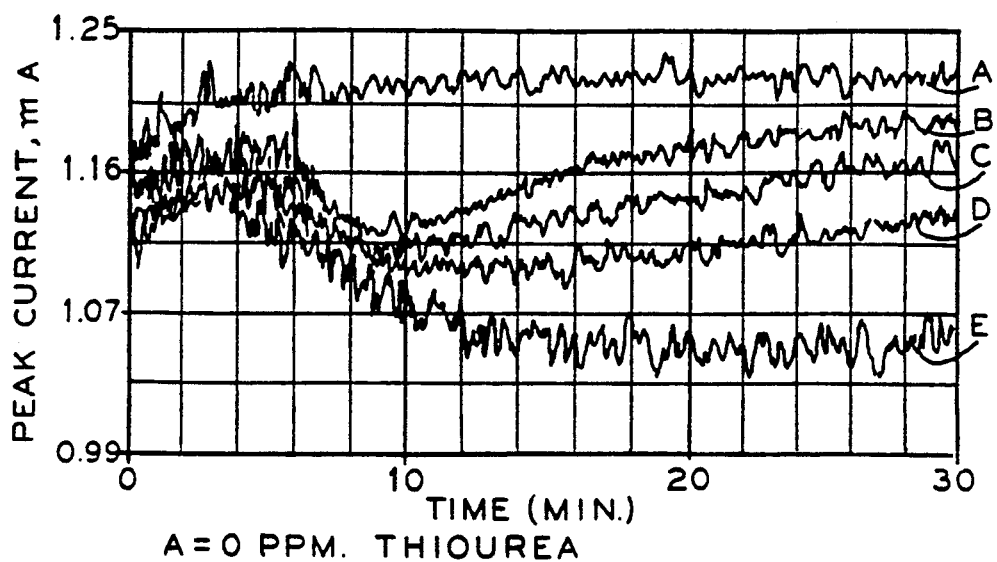
FIG. 5 is a graph of cathode peak current versus time with various concentrations of thiourea in a copper electrorefining solution.
Figure 6:
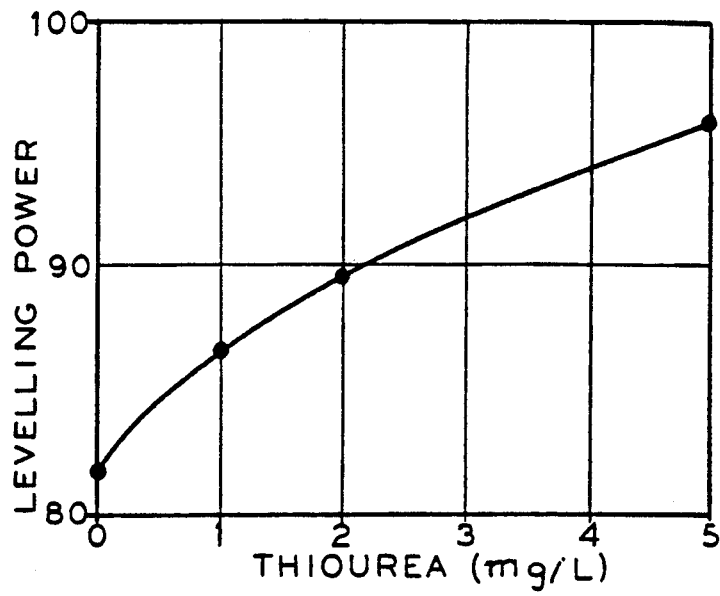
FIG. 6 is a graph of levelling power versus concentration of thiourea in a copper electrorefining solution.

A synthetic electrolyte of the same composition and temperature as in Example 1 was used. Animal glue was added to the electrolyte in such a quantity that the final concentration was 1 mg/l. Animal glue is a protein derivative formed primarily from animal skins, hides, bones and tendons. Different amounts of thiourea were then added to the electrolyte and the cathode peak current time profile was recorded. The results and parameters of the experiment are summarized in Table 2. The recorded time profiles are shown in FIG. 5. The effect of thiourea on levelling power is shown in FIG. 6. As can be seen the levelling power in the electrolyte increases with thiourea concentration.

TABLE 2

Effect of Thiourea Concentration on Cathode Peak Current and Levelling Power

| Thiourea (mg/l) | Cathode Peak Current (mA) | Levelling Power (%) |
|---|---|---|
| 0 | 1.223 | 81.5 |
| 1 | 1.187 | 87.0 |
| 2 | 1.169 | 89.9 |
| 5 | 1.133 | 95.9 |
| 50 | 1.062 | 109.0 |

Current Density = 209 A/m$^2$;
Cathode Total Current = 2.22 mA;
Plating Time = 30 min.;
Cl$^-$ = 20 mg/l;
Glue = 1 mg/l

EXAMPLE 3

Figure 7:
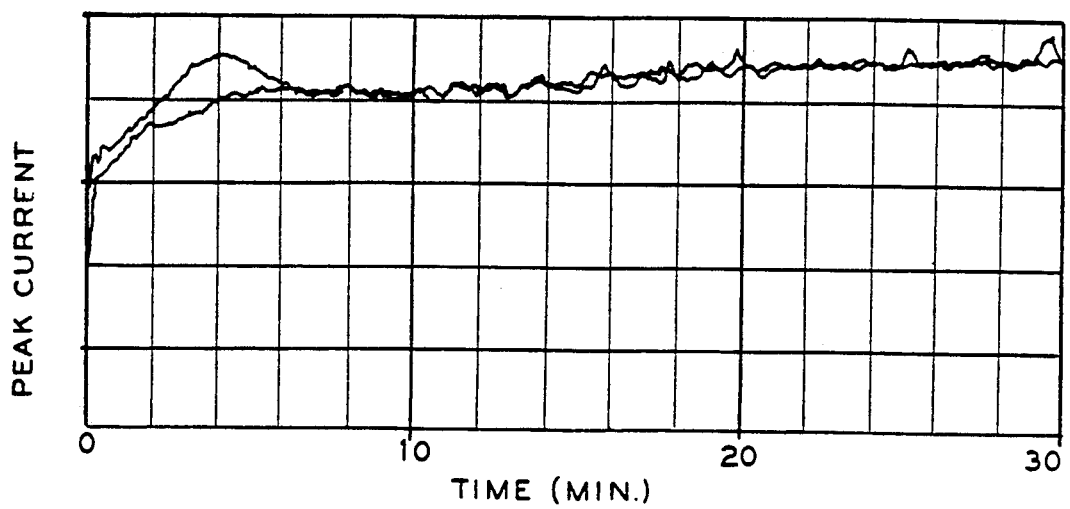
FIG. 7 is a graph of peak current versus time for two electrolytes having similar ingredients.

In this example the levelling power of electrolytes from two independent plant plating circuits for copper electrorefining were tested. The electrolytes contained 20 mg/l Cl$^-$, animal glue and Tembind. FIG. 7 illustrates that the electrolytes produced two similar cathode peak current time profiles. Therefore, since the two profiles were similar, the levelling power of both plant electrolytes were experimentally verified to be substantially identical.

In summary, the apparatus and method of the invention provide several advantages. The method of the invention provides the ability to measure the levelling power of an electrolyte. The method of the invention also reduces the time of evaluating an electrolyte system from 7 to 14 days to only 15 to 30 minutes. Finally, commercial electrolytes may be evaluated for levelling power to provide a basis for optimizing electrodeposition by adjusting electrolyte addition agents.

While in accordance with the provisions of the statute, there is illustrated and described herein specific embodiments of the invention, those skilled in the art will understand that changes may be made in the form of the invention covered by the claims and that certain features of the invention may sometimes be used to advantage without a corresponding use of the other features.

The embodiments of the invention in which an exclusive property or privilege is claimed are defined as follows:

1. A method of determining the levelling power of an electrolyte comprising the steps of:
   (a) providing an anode and a cathode within an electrolyte, said cathode having a peak region and a base region, said peak region being at least 0.5 mm closer to said anode than said base region and said peak region having a greater tendency to electrodeposit a metal per unit surface area than said base region;
   (b) applying a current between said anode and said cathode to electrodeposit the metal from said electrolyte on said cathode; and
   (c) measuring proportion of current that travels to said peak region or said base region.

2. The method of claim 1 including the additional step of:

adjusting addition agent content in said electrolyte in response to the proportion of current at said peak region or said base region.

3. The method of claim 1 including the additional step of:

reversing current to said cathode to redissolve metal into the electrolyte.

4. The method of claim 1 wherein said electrolyte is maintained at a temperature within about 5° C. of a temperature a system to be tested operates.

5. The method of claim 1 wherein said peak region and said base region are separated and electrically insulated by an insulator and wherein proportion of current travelling to said peak region or said base region is measured with said peak region and said base region of said cathode having equal surface areas.

6. The method of claim 1 wherein said current is applied with a galvanostat.

7. The method of claim 1 wherein said peak regions of said cathode project toward said anode.

8. The method of claim 1 wherein the levelling power is determined by a ratio between current at said peak region and current at said base region.

9. The method of claim 8 wherein said current is measured over a predetermined time interval.

* * * * *